United States Patent [19]

Spector

[11] Patent Number: 4,647,433
[45] Date of Patent: * Mar. 3, 1987

[54] LONG-LIFE AROMA-GENERATING CAPSULE

[76] Inventor: Donald Spector, 380 Mountain Rd., Union City, N.J. 07087

[*] Notice: The portion of the term of this patent subsequent to Jan. 8, 2002 has been disclaimed.

[21] Appl. No.: 747,936

[22] Filed: Jun. 24, 1985

Related U.S. Application Data

[63] Continuation-in-part of Ser. No. 656,768, Oct. 1, 1984, Pat. No. 4,544,592, and Ser. No. 477,353, Mar. 21, 1983, Pat. No. 4,556,539.

[51] Int. Cl.$^4$ ............................ A62B 7/08; A61L 9/02
[52] U.S. Cl. ................................... 422/125; 206/390; 362/96; 362/101
[58] Field of Search .................... 422/4, 5, 120, 123, 422/124, 125; 239/36, 53, 55, 56, 57; 362/96, 101; 206/390

[56] References Cited

U.S. PATENT DOCUMENTS

| | | | |
|---|---|---|---|
| 1,556,680 | 10/1925 | Dorment | 422/125 |
| 1,920,599 | 8/1933 | Schuh | 422/125 X |
| 2,238,476 | 4/1941 | Montieth | 422/125 X |
| 2,535,802 | 12/1950 | Libson | 422/125 |
| 2,626,833 | 1/1953 | Valentine | 239/36 X |
| 2,741,812 | 4/1956 | Tellier | 422/125 X |
| 3,386,619 | 6/1968 | Douglas | 206/390 X |
| 3,685,734 | 8/1972 | Paciorek et al. | 239/56 |
| 3,763,347 | 10/1973 | Whitaker | 422/125 X |
| 4,009,384 | 2/1977 | Holland | 422/123 X |
| 4,074,111 | 2/1978 | Hunter | 422/125 X |
| 4,161,283 | 7/1979 | Hyman | 239/55 |
| 4,277,024 | 7/1981 | Spector | 239/36 |
| 4,283,011 | 8/1981 | Spector | 239/36 |
| 4,346,059 | 8/1982 | Spector | 422/125 |
| 4,349,123 | 9/1982 | Yang | 206/390 X |
| 4,367,203 | 1/1983 | Landsberger | 422/5 X |
| 4,493,011 | 1/1985 | Spector | 422/5 X |
| 4,544,592 | 10/1985 | Spector | 239/56 X |
| 4,556,539 | 12/1985 | Spector | 422/5 X |

FOREIGN PATENT DOCUMENTS 194318  3/1924  United Kingdom .

Primary Examiner—David L. Lacey
Attorney, Agent, or Firm—Michael Ebert

[57] ABSTRACT

A long-life aroma-generating miniature capsule attachable to the surface of an incandescent light bulb to be activated by heat emanating therefrom. The capsule is constituted by a flexible pad of porous material impregnated with a volatile liquid fragrance, the pad being sandwiched between base and cover plies formed of a metal foil-plastic laminate peripherally joined together to create an envelope whose cavity is occupied by the pad. The cover ply has a vent hole therein, and the outer surface of the base ply is coated with a layer of pressure-sensitive adhesive, whereby the capsule may be conformed and adhered to the contoured surface of the light bulb. The adhered capsule is in heat transfer relation to the bulb, as a consequence of which the liquid impregnant is volatilized to produce an aromatic vapor that is discharged through the vent hole. The metal foil in the envelope acts as a heat radiator to dissipate the heat transferred thereto to a degree reducing the rate of volatilization to a level at which the capsule remains effective as an aroma generator for a prolonged period before the liquid is exhausted.

7 Claims, 5 Drawing Figures

U.S. Patent  Mar. 3, 1987  4,647,433
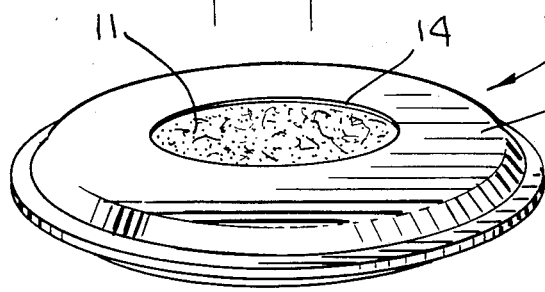
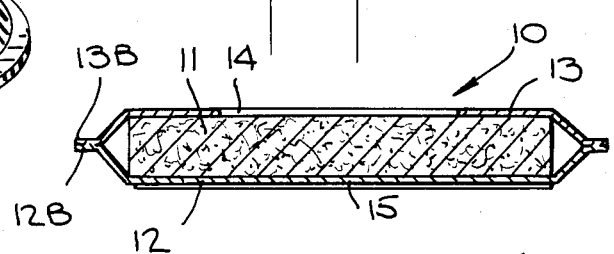
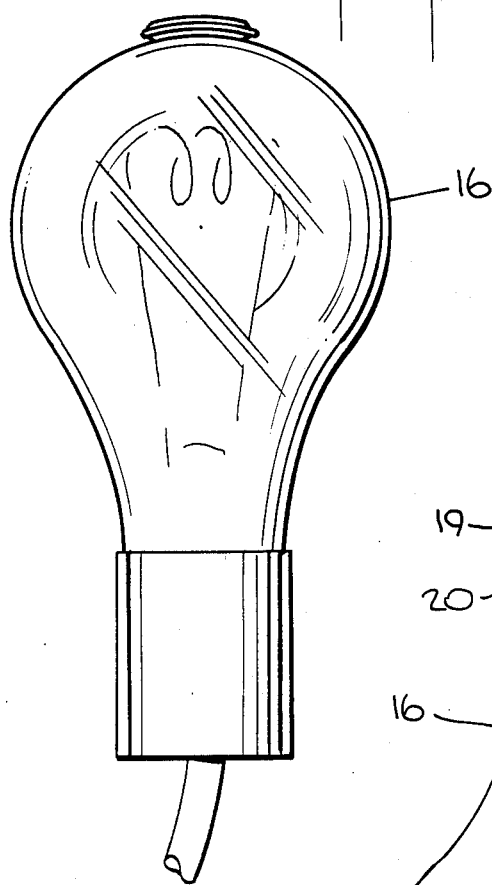
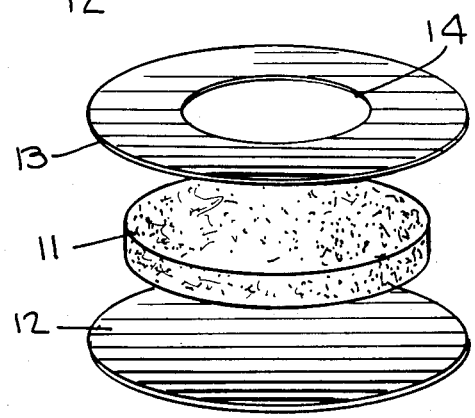
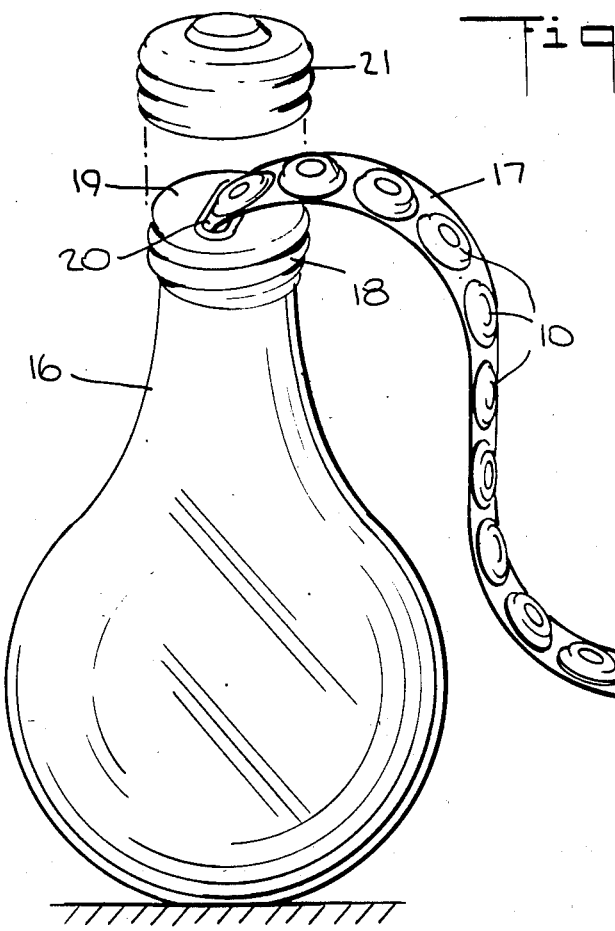
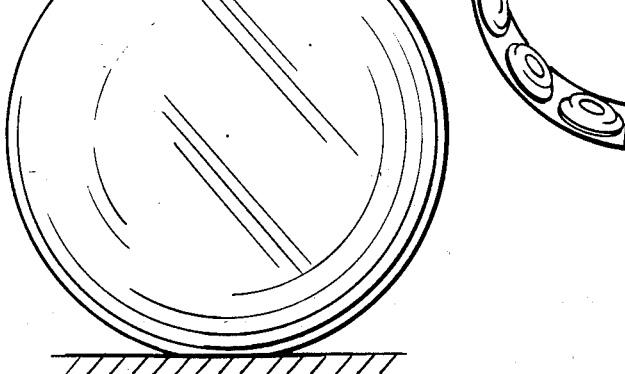

LONG-LIFE AROMA-GENERATING CAPSULE

This application is a continuation-in-part of my copending applications Ser. No. 656,768, filed Oct. 1, 1984, entitled "Aroma-Generating Capsule" (now U.S. Pat. No. 4,544,592), and Ser. No. 477,353, filed Mar. 21, 1983, entitled "Disc-Playing Aroma Generator" (now U.S. Pat. No. 4,556,539). The entire disclosures of these related applications are incorporated herein by reference.

BACKGROUND OF INVENTION

1. Field of Invention

This invention relates generally to aroma-generating devices for wafting into the atmosphere a pleasant scent or other aroma, and more particularly to an aroma-generating miniature capsule which is adhesively attachable to the surface of an incandescent light bulb to be activated by heat emanating from the bulb.

2. Prior Art

As used herein, the term "aroma" is not limited to pleasant or savory smells, but encompasses scents that function as insecticides, air fresheners, deodorants or any other odor that acts to condition, modify or otherwise charge the atmosphere.

The aroma of perfumes and perfume-based products such as colognes and toilet waters was originally derived from the essential oil of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents the ingredients are combined with alcohol.

An incandescent light bulb is an inefficient converter of electrical to light energy, for a substantial portion of the electrical energy is transformed into non-visible heat. It is for this reason that light bulbs are sometimes used as heat sources in vaporizers for suffusing a vapor into the atmosphere surrounding the bulb having medicinal, disinfecting or perfuming qualities.

Thus the Schuh U.S. Pat. No. 1,920,599 discloses a slotted disc formed of porous filter paper impregnated with a volatile solution, the disc fitting onto a light bulb. Heat radiated from the bulb brings about rapid vaporization of the impregnant. When the disc is exhausted, it may be removed from the bulb and discarded.

In the Huff U.S. Pat. No. 2,591,818, a light bulb is mounted at the base of a chimney to produce an upwardly-flowing stream of heated air which passes through a wicking element impregnated with a vaporizable liquid. In the Eisner U.S. Pat. No. 2,372,371, a porous pad saturated with a deodorant is held in a small container mounted directly on an electric light bulb. Similar bulb arrangements to promote vaporization are disclosed in the Guderman U.S. Pat. No. 1,403,548, and in the Schlesinger U.S. Pat. No. 2,437,756. All of these prior art bulb-activated aroma generators are more or less complex and relatively expensive.

Also of background interest are my prior U.S. Pat. Nos. 4,277,024; 4,346,059; 4,493,011; 4,283,011, as well as the patent to Lindenberg, U.S. Pat. No. 2,615,754.

A practical drawback encountered in heretofore known forms of aroma generators that include a liquid-impregnated pad in heat exchange relationship with a light bulb is that the heat emanating from the bulb is excessive even with a low wattage bulb. As a consequence, the liquid impregnant in the capsule is quickly volatilized and the aroma generator is effective for only a few minutes.

SUMMARY OF INVENTION

In view of the foregoing, the main object of this invention is to provide a long-life aroma-generating miniature capsule which is adhesively attachable directly onto the contoured surface of an electric light bulb, the capsule being activated by heat emanating from the bulb to discharge a scented vapor into the room illuminated by the bulb.

More particularly, an object of this invention is to provide a capsule of the above type which makes it possible for the user to quickly attach the capsule to the bulb and just as easily to detach the capsule when it is exhausted, so that the user may replace a spent capsule with another capsule yielding the same or a different aroma.

A significant feature of the invention resides in the fact that even though the capsule is directly attached to a hot light bulb, the heat applied to the internal cavity of the capsule is reduced to a degree which is sufficient to volatilize the liquid impregnant at a relatively slow rate so that the capsule remains operative for a prolonged period running several hours. In this way, the aroma exuded by the capsule into a room illuminated by the bulb is at a pleasing and acceptable level, and not overpowering as would be the case when the liquid impregnant is fully volatilized and discharged into the atmosphere in a matter of minutes.

Also an advantage of a miniature capsule in accordance with the invention is that it does not, when attached to the surface of a bulb, perceptibly interfere with the light radiated thereby. In practice, more than one capsule may be attached to a bulb at different positions thereon, the attached capsules exuding different scents to create a desired blend thereof. Thus the user, by selecting capsules providing different aromas, may become a creative blender of aromas.

Yet another object of this invention is to provide a dispenser for a supply of aroma capsules in which the capsules are adhesively mounted along a coiled strip which is uncoiled as the strip is withdrawn from the dispenser.

Briefly stated, these objects are attained in a long-life aroma-generating miniature capsule attachable to the surface of an incandescent light bulb to be activated by heat emanating therefrom. The capsule is constituted by a flexible pad of porous material impregnated with a volatile liquid fragrance, the pad being sandwiched between base and cover plies formed of a metal foil-plastic laminate peripherally joined together to create an envelope whose cavity is occupied by the pad. The cover ply has a vent hole therein, and the outer surface of the base ply is coated with a layer of pressure-sensitive adhesive, whereby the capsule may be conformed and adhered to the contoured surface of the light bulb. The adhered capsule is in heat transfer relation to the bulb, as a consequence of which the liquid impregnant is volatilized to produce an aromatic vapor that is discharged through the vent hole. The metal foil in the envelope acts as a heat radiator to dissipate the heat transferred thereto to a degree reducing the rate of volatilization to a level at which the capsule remains effective as an aroma generator for a prolonged period before the liquid is exhausted.

OUTLINE OF DRAWING

For a better understanding of the invention as well as other objects and further features thereof, reference is made to the following detail description to be read in conjunction with the accompanying drawings, wherein:

FIG. 1 is a perspective view of an aroma-generating capsule in accordance with the invention;

FIG. 2 is an enlarged section taken through the diameter of the capsule;

FIG. 3 is an exploded view of the components of the capsule;

FIG. 4 illustrates an electric light bulb having the capsule adhesively attached thereto; and FIG. 5 is a perspective view of a capsule dispenser.

DESCRIPTION OF INVENTION

Referring now to FIGS. 1 to 3, there is shown a miniature aroma-generating capsule in accordance with the invention, generally designated by reference numeral 10. The capsule includes a small diameter wafer-shaped pad 11 formed of flexible porous material having good wicking properties. Suitable for this purpose is blotting paper, open-cell flexible foam plastic material or a non-woven absorbent fabric such as cotton batting.

Pad 10 is sandwiched between an impermeable, disc-shaped base ply 12 of deformable material, and an annular cover ply 13 of the same material. The two plies have a like diameter somewhat greater than that of the pad to define circular brims 12B and 13B which extend beyond the periphery of the pad. These brims are joined together to create an envelope whose internal cavity is occupied by the pad.

The two plies 12 and 13 are formed of a deformable metal-foil plastic film laminate. In practice, the foil may be a very thin sheet of aluminum of the type conventionally used for wrapping purposes to whose faces are laminated synthetic plastic skins formed of "Mylar" polyester, polyethylene, PVC or any other plastic capable of withstanding the heat generated by the light bulb. The term "laminate" also includes plastic films which are coated in the fluid or molten state onto the faces of the metal foil.

The brims of the plies are joined together by a heat-resistant bonding agent such as an epoxy, so that the internal cavity formed within the envelope is hermetically sealed save for vent hole 14 which constitutes the only escape for the scented vapor.

Pad 10 is impregnated, preferably through vent hole 14 after the capsule is assembled, with a volatile liquid fragrance which is wicked throughout the entire body of the pad so that the pad is fully saturated. The liquid fragrance may have a fruit scent, a flower scent, or any other natural or synthetic fragrance. Thus, one may provide aroma-generating capsules in a great variety of fragrances, permitting the user to select whichever fragrance is appropriate for a given occasion. The invention is not limited to pleasing scents, and capsules may be impregnated to function as deodorizers, as insect repellents or as disinfectants. In order to distinguish different scents, the plastic in the plies may be pigmented or dyed in different colors, thereby providing color coded capsules in which red, say, identifies a rose-like smell, yellow a lemon smell, etc.

The undersurface of the base ply 12 is coated with a low-tack, pressure-sensitive adhesive layer 15 which is heat resistant. For this purpose, an elastomeric mass coat may be used that will afford a bond of moderate strength upon application of only light pressure.

When capsule 10 is adhesively attached to the contoured surface of a light bulb 16, as shown in FIG. 4, because its envelope is deformable, the capsule will conform to the surface of the bulb regardless of where it is placed. When the capsule is exhausted, it may be peeled off the lamp and discarded.

In practice, each capsule may be provided with a removable sticker to seal vent hole 14 on cover ply 13 and thereby prevent the loss of scent when the capsule is being stored, so that the capsule has a prolonged storage life. Base ply 12 may be provided with a peel-off disc to protect the sticky adhesive layer 15.

Instead of using a peel-off protective disc for each capsule, a train of capsules 10 may be mounted on a carrier strip 17 of paper or plastic film, as shown in FIG. 5, having a smooth coated face surface onto which the capsules are adhesively attached. The nature of the coated face is such that the capsules may be readily released therefrom.

The strip 16 and the capsules 10 mounted thereon are coiled into a roll which is housed within a dispenser 17 which generally assumes the shape of a light bulb, except that the base of this dispenser is flat, so that it can rest on a table or other flat surface. The threaded neck 18 of the dispenser is closed by a plate 19 having a discharge slot 20 therein through which the strip is drawn.

Also provided is a cap 21 which is adapted to screw onto threaded neck 18 of the dispenser, the cap having an interior cavity to accommodate the exposed tail of strip 17. Thus, if a user wishes to extract from the dispenser five capsules, he unscrews the cap and pulls out the strip to expose six capsules. He then removes the required five capsules and snips off the strip, leaving a tail with the remaining capsule, which lies within the cap when the cap is screwed back on the neck of the dispenser. In this way, there is no need to provide each capsule with a peel-off sticker to prevent the loss of fragrance in storage, for the capsules on the coiled roll are normally collectively sealed within the dispenser.

Because the liquid-impregnated pad 10 occupies the internal cavity of an envelope which is sealed save for the vent hole 14 in the upper ply, air is entrapped in the interstices of the fibers forming the pad. As a consequence, when the capsule is adhered to the contoured surface of the light bulb in heat transfer relation therewith, the transferred heat acts to volatilize the liquid fragrance which impregnates the fibers to produce an aromatic vapor. At the same time it heats and expands the entrapped air to produce a positive pressure which acts to force the scented vapor out of vent hole 14 into the atmosphere.

The rate at which vapor is discharged from the vent hole depends on the level of heat energy applied to the entrapped air and the liquid fragrance in the envelope cavity. Because the envelope is formed of a metal foil laminate having a high degree of thermal conductivity, the exposed surface of the envelope acts as a heat radiator which dissipates the heat into the atmosphere and reduces the level of heat transferred to the internal cavity. This acts to slow down the rate at which an aromatic vapor is generated by the capsule and prolongs its effective life. As a consequence, the capsule remains operative as an aroma generator for several hours, rather than for a few minutes, as would be the case had the envelope been formed of a non-metallic material.

While there has been shown and described a preferred embodiment of LONG-LIFE AROMA-GENERATING CAPSULE in accordance with the invention, it will be appreciated that many changes and modifications may be made therein without, however, departing from the essential spirit thereof. Thus to enhance the heat radiating surface of the capsule, the cover ply thereof may be in a corrugated formation.

I claim:

1. In combination, an incandescent light bulb having a contoured surface and an aroma-generating miniature capsule attached to the contoured surface of said incandescent light bulb to be activated by heat emanating therefrom, the capsule comprising:
   A. a flexible pad of porous material impregnated with a volatile aromatic liquid;
   B. an envelope formed by an imperforate base ply and a cover ply having a vent hole therein, the margins of the plies being joined together to define an internal cavity which is sealed save for the vent hole, said plies being formed of a deformable metal-foil plastic film laminate having a high degree of thermal conductivity, the plastic film in said laminate being of a material capable of withstanding the heat generated by the bulb, the pad occupying said cavity whereby air as well as the liquid impregnant is entrapped therein; and
   C. a layer of heat-resistant, pressure-sensitive adhesive coated on the exposed surface of the base ply whereby the capsule is conformed and adhesively attached to the contoured surface of the bulb in heat transfer relationship thereto, as a result of which the liquid impregnant is volatilized to produce an aromatic vapor and the entrapped air is heated and expanded to produce positive pressure forcing the vapor out of the vent hole and discharging it into the atmosphere, said metal foil in the envelope acting as a heat radiator to dissipate heat into the atmosphere and thereby reduce the heat transferred to the cavity to a degree causing a slow down in the rate of vapor discharge whereby the capsule is effective as an aroma generator for a prolonged period.

2. A combination as set forth in claim 1, wherein said metal foil is aluminum.

3. A combination as set forth in claim 1, wherein the plastic film is polyester.

4. A combination as set forth in claim 1, wherein said pad is formed of blotting paper.

5. A combination as set forth in claim 1, wherein said liquid impregnant is a perfume.

6. A combination as set forth in claim 1, wherein said pad is wafer-shaped and has a small diameter, said plies being disc-shaped and having a larger diameter then said pad to form circular margins which extend beyond the periphery of the pad and are joined together.

7. A combination as set forth in claim 1, wherein said film has a distinctive color, whereby capsules may be color-coded to identify their aromas.

* * * * *